(12) United States Patent
Cecchetto et al.

(10) Patent No.: US 11,753,372 B2
(45) Date of Patent: Sep. 12, 2023

(54) PROCESS FOR THE PRODUCTION OF EPSILON CAPROLACTAM FROM 6-AMINOCAPROIC ACID

(71) Applicants: AQUAFIL S.P.A., Arco (IT); GENOMATICA INC., San Diego, CA (US)

(72) Inventors: Michele Cecchetto, Arco (IT); Anacleto Dal Moro, Arco (IT); Lauri Hannunpoika Suominen, San Diego, CA (US); Michael Japs, San Diego, CA (US)

(73) Assignees: AQUAFIL S.P.A., Arco (IT); GENOMATICA INC., San Diego, CA (US)

( * ) Notice: Subject to any disclaimer, the term of this patent is extended or adjusted under 35 U.S.C. 154(b) by 163 days.

(21) Appl. No.: 17/418,060

(22) PCT Filed: Dec. 23, 2019

(86) PCT No.: PCT/IB2019/061270
§ 371 (c)(1),
(2) Date: Jun. 24, 2021

(87) PCT Pub. No.: WO2020/136547
PCT Pub. Date: Jul. 2, 2020

(65) Prior Publication Data
US 2022/0089536 A1    Mar. 24, 2022

(30) Foreign Application Priority Data
Dec. 28, 2018 (IT) .................. 102018000021409

(51) Int. Cl.
*C07D 201/08* (2006.01)
(52) U.S. Cl.
CPC .................................. *C07D 201/08* (2013.01)
(58) Field of Classification Search
CPC .................................................. C07D 201/08
See application file for complete search history.

(56) References Cited

U.S. PATENT DOCUMENTS

| | | |
|---|---|---|
| 3,485,821 A | 12/1969 | Sheehan et al. |
| 3,658,810 A | 4/1972 | Tanaka et al. |
| 4,599,199 A | 7/1986 | Fuchs |
| 4,767,856 A | 8/1988 | Dockner et al. |
| 6,194,572 B1 | 2/2001 | Buijs et al. |
| 6,333,412 B1 * | 12/2001 | Guit ............... C07D 201/08 540/538 |
| 10,787,417 B2 * | 9/2020 | Dal Moro ............ B01D 3/10 |
| 11,208,380 B2 * | 12/2021 | Dal Moro ........... C07D 201/16 |

FOREIGN PATENT DOCUMENTS

| | | |
|---|---|---|
| WO | 2005068643 A2 | 7/2005 |
| WO | 2010129936 A1 | 11/2010 |
| WO | 2011078668 A1 | 6/2011 |

OTHER PUBLICATIONS

International Search Report dated Mar. 18, 2020 re: Application No. PCT/IB2019/061270, pp. 1-3, citing: US 3 485 821 A, US 3 658 810 A and WO 2011/078668 A1.
Written Opinion dated Mar. 18, 2020 re: Application No. PCT/IB2019/061270, pp. 1-5, citing: US 3 485 821 A, US 3 658 810 A and WO 2011/078668 A1.

* cited by examiner

*Primary Examiner* — Golam M Shameem
(74) *Attorney, Agent, or Firm* — CANTOR COLBURN LLP

(57) ABSTRACT

A new process for the production of epsilon caprolactam (CPL) from 6-aminocaproic acid (6-ACA) can be obtained either from traditional petro chemical processes or can be obtained from biochemical processes. With the proposed process, the reaction time for conversion of 6-aminocaproic acid to the Nylon 6 monomer is shorter and significant energy savings are possible which is advantageous for industrial scale production. The conversion of 6-aminocaproic acid to the Nylon 6 monomer runs at atmospheric pressure and in the final product epsilon caprolactam with no oligomers formation of significance is obtained.

30 Claims, 2 Drawing Sheets

PROCESS FOR THE PRODUCTION OF EPSILON CAPROLACTAM FROM 6-AMINOCAPROIC ACID

Figure 1:
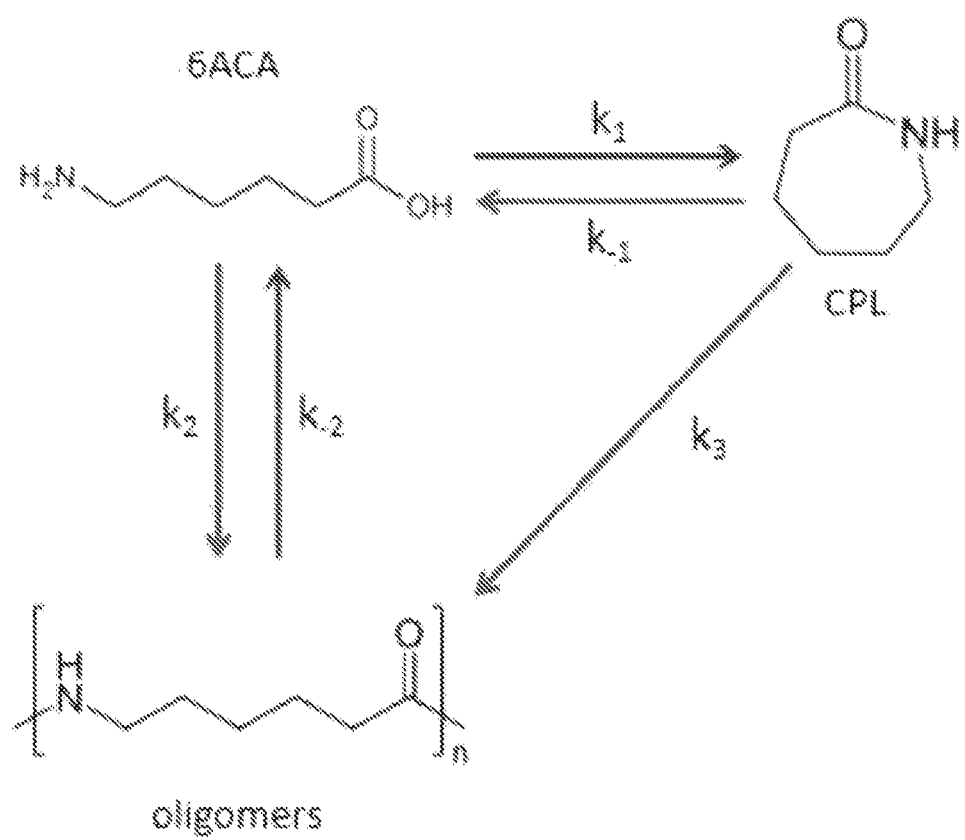

The project leading to this application has received funding from the Bio Based Industries Joint Undertaking (JU) under the European Union's Horizon 2020 research and innovation programme under grant agreement No 792195. The JU receives support from the European Union's Horizon 2020 research and innovation programme and the Bio Based Industries Consortium.

TECHNICAL FIELD

The present disclosure refers to a new process for the production of epsilon caprolactam (CPL) from 6-aminocaproic acid (6-ACA) wherein 6-aminocaproic acid is converted to epsilon caprolactam, which is a monomer to synthesise Nylon 6. The process is suitable for the starting material which comprises 6-aminocaproic acid produced from petroleum raw material source or from a renewable source like sugars including first and/or second generation type, i.e. bio based 6-ACA. The final product obtained is a water solution of epsilon caprolactam free of oligomers, with properties which correspond to the properties of epsilon caprolactam obtained by traditional way (i.e. by the reaction known as the "Beckmann rearrangement"). Further with the proposed process the reaction time for conversion of 6-aminocaproic acid to the Nylon 6 monomer is shorter and significant energy savings are possible which is advantageous for industrial scale production. So produced solution of epsilon caprolactam can be further submitted to known purification steps to obtain a monomer suitable for polymerization into Nylon 6.

BACKGROUND

Caprolactam is the lactam of 6-aminocaproic acid (or 6-ACA or 6-aminohexanoic acid). Its production and purification are of great relevance, since caprolactam is the monomer used in the production of polyamide 6, commonly known as Nylon 6.

Caprolactam is generally obtained by the reaction known as the "Beckmann rearrangement", by means of which cyclohexanone oxime in liquid state is converted into caprolactam by a mixture of sulphuric acid/SO3 (i.e. oleum). After neutralization with ammonia and separation of the ammonium sulphate salt, so obtained solution of caprolactam is further submitted to known purification steps to obtain a monomer suitable for polymerization into Nylon 6.

Literature exists where different processes are described wherein caprolactam is produced from 6-aminocaproic acid or 6-aminocaproamide or 6-aminocaproate ester or their mixtures.

U.S. Pat. No. 6,194,572 describes a process to prepare epsilon caprolactam by treating 6-aminocaproic acid, 6-aminocaproate ester or 6-aminocaproamide or their mixtures in the presence of superheated steam in which a gaseous mixture comprising epsilon caprolactam is reportedly obtained. The process is carried out in the absence of catalyst at a temperature between 250 and 400° C. and at a pressure of between 0.5 and 2 Mpa, i.e. above atmospheric pressure.

U.S. Pat. No. 3,485,821 reports that caprolactam is produced by heating 6-aminocaproic acid or 6-aminocaproamide with water or aqueous solution, the concentration of the starting material is from 5 wt. % to 25 wt. % and the temperatures are from 150 to 350° C. It reports that caprolactam is produced in quantitative yield at high conversion with substantially no contamination with polymers; however the proposed process is suitable for low concentrations of the starting material and thus is not industrially efficient and furthermore, 6-aminocaproic acid is not completely converted to Nylon 6 monomer.

U.S. Pat. No. 4,599,199 reports that caprolactam is obtained by treating ε-aminocaproic acid with steam at elevated temperatures in the presence of a catalyst by a process in which ε-aminocaproic acid is introduced into a fluidized alumina bed, wherein gamma-alumina with particle size of 0.2 to 1 mm was reported as a particularly useful catalyst, and treated in the presence of steam at from 290° to 400° C.

U.S. Pat. No. 4,767,856 reported that caprolactam is prepared by heating 6-aminocaproic acid, an ester or amide or mixture thereof in the presence of an inert reaction medium which is liquid under the reaction conditions and has a boiling point above that of caprolactam, the alleged improvement comprises using as the reaction medium a hydrocarbon, maintaining a temperature of from 150° to 350° C., charging the 6-aminocaproic acid, ester, amide or mixture thereof at a rate commensurate with their rate of conversion, and separating caprolactam from the reaction mixture at a rate commensurate with its rate of formation. The process uses reduced pressure. An acid catalyst was proposed to be used additionally with the inert reaction medium, which are liquid hydrocarbons, for example mineral oil fractions.

In U.S. Pat. No. 3,658,810 the technical problem was to develop new process for the preparation of epsilon caprolactam without formation of ammonium sulphate which was the main concern at that time. Said patent reports caprolactam is produced by contacting with steam 6-amminocaproic acid or caproamide at temperature 150-400° C. preferably using a non-volatile acid catalyst. All the presented experiments were conducted at a laboratory scale using few grams of materials. As can be seen from its examples if the starting material comprising a solution of 6-aminocaproic acid in water was used, the concentration reportedly was never above 30 wt. %, and if the starting material comprising 6-aminocaproic acid in an isolated form was used, reportedly the yield was always below 90% when atmospheric pressure or slightly reduced pressure was used. Reportedly the yield slightly increased only at elevated pressure but still 6-aminocaproic acid is not converted to Nylon 6 monomer as efficiently as it is in the process according to the present disclosure described herein. In view of the above-mentioned facts, including the limited laboratory small-scale work, the reported process of U.S. Pat. No. 3,658,810 is to be considered more similar to scientific literature, and its use in the real industrial scale is not demonstrated.

In view of the drawbacks in the above mentioned cyclization processes, efficient methods for industrial preparation of epsilon caprolactam are still needed. The above mentioned processes require low concentrations of 6-ACA (aqueous solutions containing in general not more than 30 percent by weight of 6-ACA on the total mass of the starting material, more often around 10%), the processes require the use of high temperature and/or high or reduced pressure (above or below atmospheric pressure) and/or the use of catalysts which are usually metals or metal oxides or heterogeneous catalysts and/or the use of organic solvents. Even if the catalyst is used as described in the U.S. Pat. No. 3,658,810, the reported yield is well below 100%, in general at level of 70-80%, and in the final recovered product high level of not-converted 6-aminocaproic acid and its oligomers together with many others unknown by-products is reported. 6-Aminocaproic acid is not completely converted to Nylon 6 monomer as it is in the process according to the present disclosure as described herein.

More recently, the 6-ACA became industrially available from traditional petro chemical processes and is also available from renewable sources, i.e. bio based 6-ACA. For example, in WO2005/068643 and WO 2010/129936 the process for preparation of 6-aminocaproic acid in the presence of an enzyme is disclosed.

In WO 2011/078668 a preparation of caprolactam from the starting material comprising 6-aminocaproic acid obtained in fermentation process in the presence of superheated steam is disclosed. The application is a significant improvement to the preparation process as disclosed in U.S. Pat. No. 6,194,572 or 3,658,810. However, the process gives satisfactory yields when the weight to weight ratio carbohydrate to 6-aminocaproic acid in the starting material is 0.03 or less. When higher amounts of carbohydrates are present the reported yield is below 70%. Further the process reports using higher pressure, above atmospheric pressure.

SUMMARY

To propose a process for the transformation of 6-aminocaproic acid which can be used at industrial scale is now becoming of importance and interest.

The present disclosure therefore provides a process for the production of epsilon caprolactam from 6-aminocaproic acid which can be obtained either from traditional petro chemical processes or which can be obtained from biochemical processes, at industrial scale which overcomes the drawbacks of the known processes. When 6-aminocaproic acid obtained from biochemical processes is used in a starting material carbohydrate-derived epsilon caprolactam is produced.

Thus the present disclosure also provides a process for preparing carbohydrate-derived epsilon caprolactam wherein a mixture containing 6-aminocaproic acid is recovered from a culture medium comprising biomass, wherein the culture medium comprises one or more carbohydrates and contaminants coming from fermentation during the production of the bio-based 6-ACA.

The present disclosure further provides a process for production of epsilon caprolactam from 6-aminocaproic acid which uses the atmospheric pressure and whereby 6-aminocaproic acid is converted, preferably completely converted, to epsilon caprolactam with no oligomers formation of significance in the final product, i.e. in a water solution of epsilon caprolactam, neither from the initial linear 6-ACA, neither from the obtained cyclic epsilon caprolactam. Further with the proposed process the reaction time for conversion of 6-aminocaproic acid to the Nylon 6 monomer is shorter and significant energy savings are possible and no organic solvents are used which is advantageous for industrial scale production.

BREIF DESCRIPTION OF THE DRAWINGS

Figure 2:
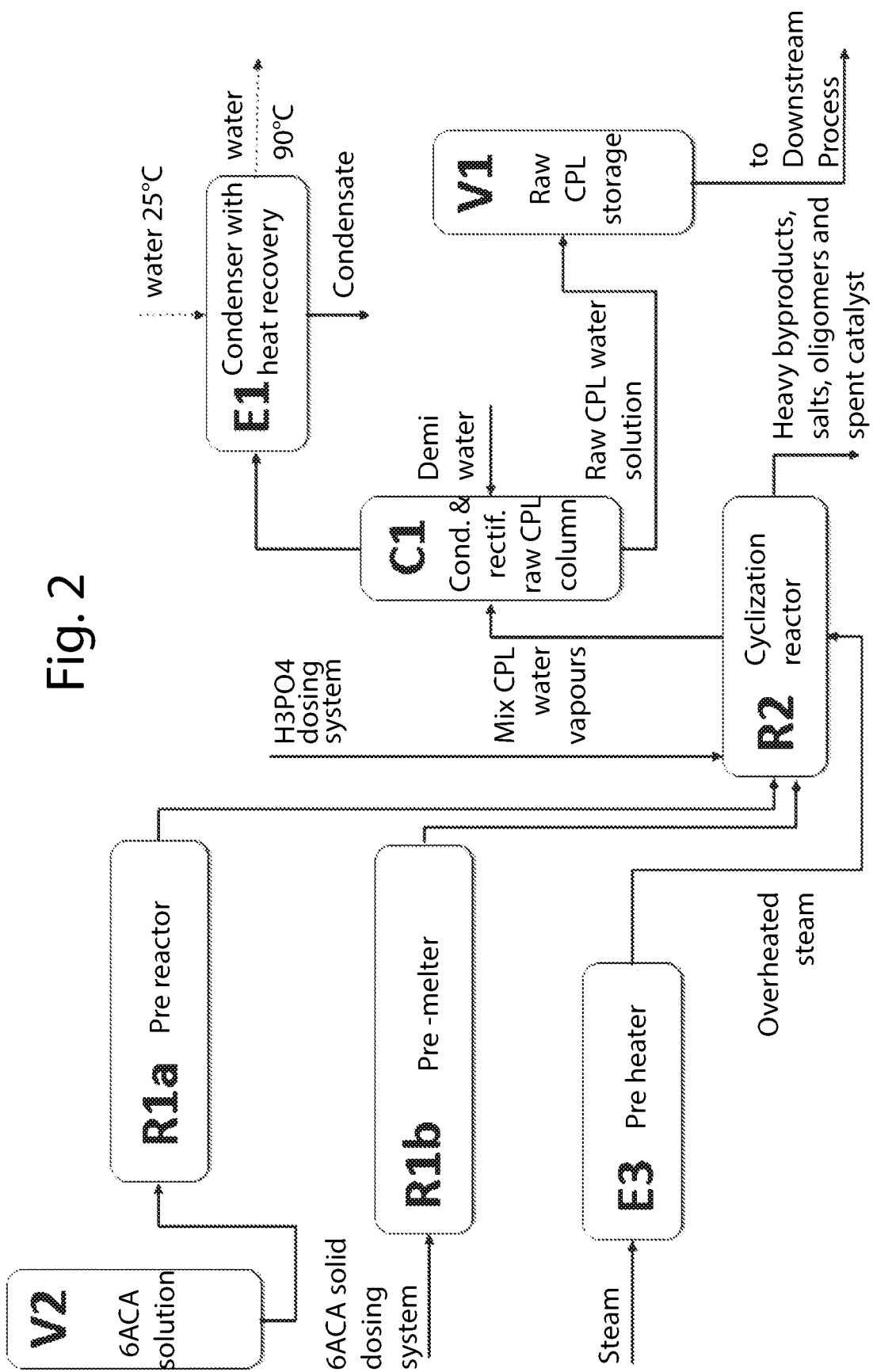

The features and advantages of a process for the production of epsilon caprolactam from 6-aminocaproic acid will be more apparent from the following description, which is to be understood as exemplifying and not limiting, with reference to the drawings, wherein:

FIG. 1 shows possible reactions indicated by arrows with respect to chemical species present in the mixture; and FIG. 2 shows a block diagram of the process for the production of epsilon caprolactam from 6-aminocaproic acid according to the disclosure.

DETAILED DESCRIPTION OF THE DISCLOSURE

The disclosure will be explained in greater detail hereinafter and presented in FIG. 2, which shows block diagram of the process for the production of epsilon caprolactam from 6-aminocaproic acid according to the disclosure.

A process for the production of epsilon caprolactam from 6-aminocaproic acid comprising the following steps:

step (i)—pre-treating a starting material comprising 6-aminocaproic acid in order to prepare it for step (ii)—the cyclization, whereby the starting material is pre-heated to the temperature in or near the temperature of a cyclization reactor of step (ii) to accelerate a cyclization reaction in step (ii), which can provide an advantage to avoid by-products formation and loss of yield;

step (ii)—feeding the pre-treated starting material obtained in step (i) under a controlled flow rate into a cyclization reactor and continuously contacting said starting material with a constant flow of superheated steam in the presence of a catalyst, wherein cyclization of 6-aminocaproic acid to epsilon caprolactam occurs, wherein the cyclization reactor is at a pressure and temperature favouring cyclization and steam-stripping and wherein stream-stripping of a vapor mixture comprising epsilon caprolactam and water occurs continuously with the superheated steam, and whereby the 6-aminocaproic acid is converted at equal to or greater than 95%, 96%, 97%, 98%, 99%, 99.5%, 99.9% or 100% to epsilon caprolactam and whereby vapor mixture comprising epsilon caprolactam and water is free of oligomers;

step (iii)—condensing the vapour mixture comprising epsilon caprolactam and water obtained from step (ii) to obtain an aqueous solution of epsilon caprolactam which is optionally further concentrated and optionally further purified according to known methods, for example by distilling. Free of oligomers means, depending on the conversion percentage of 6-ACA to epsilon caprolactam, a percentage of oligomers by weight less than or equal to 5%, 4%, 3%, 2%, 1%, 0.5%, 0.1% or 0%, or undetectable by the analytical method described herein.

Pre-treatment of the starting material comprising 6-aminocaproic acid in step (i) is advantageous since in said step the starting material is pre-heated to the desired temperature before entering the cyclization step (ii). Thus the cyclization reaction in step (ii) is accelerated and starts almost instantly right after the pre-treated starting material enters the cyclization reactor. Due to the pre-heating of the starting material there is no time delay before the cyclization reaction actually starts, which is the case if starting material comprising 6-aminocaproic acid is fed directly into the cyclization step (ii) without the pre-treatment step (i). Another advantage is that with the pre-treatment, the flow rate of the pre-treated material which is fed from step (i) to step (ii) is easily controlled in order to maintain the amount of linear 6-aminocaproic acid inside the cyclization reactor at a desired value to avoid possible side reaction and loss of yield s as will be explained hereinafter.

Since the starting material comprising 6-aminocaproic acid which is used in the proposed process can be in a form of a solution of 6-aminocaproic acid in water with the concentration of 6-aminocaproic acid at least 50 wt. % on the total mass of the starting material, or the staring material comprises 6-aminocaproic acid in an isolated powdered form, there are two different ways to pre-treat the starting material comprising 6-aminocaproic acid.

With respect to FIG. 2 pre-treatment of the starting material comprising 6-aminocaproic acid in a form of a solution in water with the concentration of 6-aminocaproic acid at least 50 wt. % on the total mass of the starting material is done in a pre-reactor R1a. A solution of 6-aminocaproic acid in water with the concentration of at least 50 wt. % is loaded from a storage vessel V2, where it is held preferably at a temperature in the range from 50-80° C., into a pre-reactor R1a. In another embodiment 6-aminocaproic acid in a solid state and water in quantities that provide the above mentioned concentration of solution of 6-aminocaproic acid in water, are directly fed into the pre-reactor R1a. Suitable pre-reactor is any reactor allowing increasing the temperature of the feed solution to the desired temperature, preferably a closed adiabatic reactor which provides anadiabatically isolated system in the reactor. Said starting material is then pre-heated to the temperature in or near the temperature of a cyclization reactor of step (ii), preferably to the temperature in the range from 170-260° C., more preferably to a temperature in the range from 190-200° C. Since there is no exchange of matter with the outside, the formation of vapours causes an increase of pressure up to 8-10 bars. When the conditions above are met, the solution is held under these conditions for at least 30 minutes. In such a prepared solution, water is in condition to flash immediately and to be transformed into steam, when said solution is fed into the cyclization reactor of step (ii). Since the starting material is already pre-heated, the cyclization reaction in step (ii) starts almost instantly, i.e. the residence time of 6-aminocaproic acid before it undergoes the cyclization reaction in step (ii) is minimized, and possible by-products formation (mainly oligomers) and loss of yield are avoided.

These conditions are assuring that all linear 6-aminocaproic acid in water is dissolved, including some potential oligomers that could be formed from the linear 6-aminocaproic acid in such a way that both, the linear 6-aminocaproic acid itself and the potential oligomers, are easily transformed into cyclic caprolactam in the next step (ii) at atmospheric pressure.

Pre-treatment can be done in batch mode or in continuous mode. For a continuous process a flow regulation of solution of in water "in" and "out" of the pre-reactor is to be maintained in such a way that the residence time of the solution of 6-aminocaproic acid in water under the conditions defined above, is at least 30 minutes.

So obtained material is transferred to the following step (ii) into the cyclization reactor where the cyclization occurs.

The pre-reactor can be made of any suitable material capable of withstanding temperature, pressure and acid conditions inside the reactor. Preferably the pre-reactor is made of stainless steel. A dosing system for feeding the starting material into the reactor is provided, preferably in the upper part of the reactor, and an exit opening for transferring the pre-heated solution by a piping into the cyclization reactor of step (ii) under a controlled flow rate is provided, preferably in the lateral side at the bottom. The upper part of the reactor, where the vapors phase is maintained, is connected with a pressure safety valve to avoid the pressure increase over a fixed limit. To supply the necessary heat for pre-heating, the reactor is externally heated by suitable means, for example via a heating jacket or heating coils with suitable heating media. In a preferred embodiment the outside walls of the reactor are covered by an external jacket with thermal oil.

Optionally a removable filter is provided either inside the reactor or within the exit opening, to filter off and remove from time to time, if necessary, some not dissolved starting material. This is predominantly in the case of bio based 6-aminocaproic acid used in a starting material which can contain some residual materials from fermentation process, i.e. the residual renewable raw materials or other 6-aminocaproic acid contaminants coming from the bio process.

As alternative pre-treatment process when the starting material comprises 6-aminocaproic acid in an isolated powdered form, the pre-treatment is done in a pre-melter R1b. 6-aminocaproic acid in an isolated powdered form is fed directly as a powder (for example, with a screw system) into a pre-melter and then pre-heated to a temperature higher than the melting point of 6-aminocaproic acid, i.e. above 205° C., preferably to a temperature in the range from 210-260° C., thus a molten 6-aminocaproic acid with no water is obtained. There is no need to keep the pre-melter under pressure, but a slight pressure of nitrogen is preferred to avoid unwanted effects given by the presence of air, i.e. oxidation of impurities, for example valeramide, adipimide, that could affect the quality of the caprolactam in its final use. Preferably the starting material can be fed into the pre-melter continuously and is also transferred into the cyclization reactor of step (ii) continuously.

So obtained material is transferred to the following step (ii) into the cyclization reactor where the cyclization occurs.

In a preferred embodiment the starting material comprises 6-aminocaproic acid in a form of a solution in water with the concentration of 6-aminocaproic acid at least 50 wt. %, based on the total mass of the starting material. As already mentioned said 6-aminocaproic acid can be obtained either from traditional petro chemical processes or can be obtained from biochemical processes, wherein higher amounts of carbohydrates and other contaminants coming from fermentation during the production of the bio-based 6-ACA are comprised in 6-aminocaproic acid. With the proposed process the 6-aminocaproic acid starting material can optionally comprise at least 12.5 wt. %, 10 wt. %, 5 wt. %, 4 wt. %, 3.5 wt. %, 3.4 wt. %, 3 wt. %, 2 wt. % or 1 wt. % and up to 15 wt. %, 12.5 wt. %, 10 wt. %, 5 wt. % or 4 wt. % of carbohydrate, based on the mass of the 6-aminocaproic acid.

In step (ii) the cyclization of 6-aminocaproic acid comprised in the starting material occurs continuously in a cyclization reactor R2. By contacting 6-aminocaproic acid with a flow of superheated steam and in the presence of a catalyst, vapours of mixture of epsilon caprolactam and water are formed which are continuously stripped off with the flow of the superheated steam, thus the cyclization reactor is not a closed system. The cyclization reactor works at atmospheric pressure or at slightly elevated pressure, i.e. in the range from 1.0 to 1.5 bar, and at temperature in the range from 220 to 350°. Preferably the cyclization reactor works at atmospheric pressure or at slightly elevated pressure, i.e. in the range from 1.0 to 1.5 bar. The temperature of superheated steam in preferably kept in the range from 300-450° C.

Namely inside the cyclization reactor a lot of chemical species could be present in the mixture, but three are most critical: 6-aminocaproic acid (6ACA), caprolactam (CPL) and oligomers.

They are related to one another by the reactions indicated in FIG. 1 wherein the arrows represent possible reactions:

$k_1$: cyclization of 6ACA to CPL;
$k_{-1}$: ring opening of CPL (to obtain 6ACA);
$k_2$: polymerization of 6ACA to oligomers;
$k_{-2}$: depolymerization of oligomers to 6ACA;
$k_3$: polymerization of CPL to oligomers.

The depolymerization of oligomers back to caprolactam must pass through 6-aminocaproic acid.

Of course the reaction rates are different, but all the reactions can happen at the same time. So in a closed system all three chemical species are present all together in the reactor.

It is also convenient and necessary to maintain the conditions inside the cyclization reactor in such a way that the formation of liquid water (H2O) in the reacting mass is minimized or preferably avoided as the reaction of caprolactam back to 6-ACA is defined by the equilibrium:

$$6\text{-ACA} \rightleftarrows \text{CPL} + \text{H2O}$$

In the proposed process the system in the cyclization reactor is not a closed system due to the continuous flow of the superheated steam into the cyclization reactor and the continuous stripping away of vapours of caprolactam and water from the cyclization reactor, thus by constant removal of caprolactam, the equilibrium between caprolactam and linear 6-aminocaproic acid is continuously and completely shifted to the right, thus the formation of caprolactam is fast and the linear 6-aminocaproic acid is preferably completely converted to caprolactam.

The cyclization reactor can be made of any suitable material resistant to strong acids at high temperature. Preferably the cyclization reactor is made of stainless steel, like Stainless Steel with Ti or some alloy like Hastelloy or Inconel type.

The cyclization reactor is equipped with a dosing system, preferably nozzles, for feeding the catalyst, preferably liquid and which is more preferably a concentrated water solution of an acid compound, into the reactor. Preferably the nozzles are provided at or near the top of the cyclization reactor. An exit of the vapor mixture of caprolactam and water which is led through a pipeline into step (iii) is provided at or near the top of the cyclization reactor. Optionally at or near the bottom of the cyclization reactor means for purging are provided, to purge off, when necessary, the sludge/tars coming from heavies and contaminants coming from possible degradation of the organic materials, predominantly in the case of bio based 6-aminocaproic acid used in the process.

To provide the necessary heat for the cyclization process, the reactor is heated by suitable means, for example via a heating jacket or heating coils with a suitable heating media, preferably externally. In a preferred embodiment the outside walls of the reactor are covered by an external jacket with thermal oil.

The cyclization reactor is further equipped with safety valves to control and to keep the pressure at the atmospheric value or at slightly elevated pressure, i.e. in the range from 1.0 to 1.5 bar.

Of course the cyclization reactor can be provided with all the required instrumentation for continuous temperature measurement, heating, flows, level controls and so on.

The cyclization reactor is further equipped with a dosing and distribution system for superheated steam. In a preferred embodiment superheated steam enters the cyclization reactor through nozzles on top of the cyclization reactor and continues through pipes inside the reactor to the distribution system executed at the bottom of the cyclization reactor, to enable and maintain homogenous and continuous stirring of the mixture, which consists of liquid/molten phase and vapors phase. Thus the continuous stirring of the mixture, which provides and maintains full homogeneous system needed for smooth and controlled cyclization process, is enabled by superheated steam, so no mechanical stirring system is needed.

In a preferred embodiment, the superheated steam is continuously fed through an annular series of steam jets located at the bottom of the cyclization reactor. This arrangement guarantees an effective stirring inside the cyclization reactor.

In a preferred embodiment, when the cyclization reactor is fed with the solution obtained in the pre-reactor R1a, said solution is fed into the cyclization reactor through nozzle, preferably lateral, provided at the bottom of the cyclization reactor. Namely said solution contains water and the flash of water should always happen in the mixture inside the cyclization reactor, preferably at the bottom part of the cyclization reactor.

In another embodiment, when the molten material from the pre-melter R1b is fed into the cyclization reactor, this can be done through the nozzle provided on the top of the cyclization reactor, since the molten material contains no water and no flash of water occurs.

Preferably, in order for the cyclization reaction to run smoothly and controllably, the cyclization reactor is, for the start-up phase, brought to the working conditions, i.e. to the selected temperature, selected flow of superheated steam and selected catalyst concentration, before the pre-treated starting material comprising 6-aminocaproic acid from step (i) is fed into the cyclization reactor of step (ii).

For the start-up phase the cyclization reactor is fed with the initial load of caprolactam solution and the catalyst. Caprolactam solution is for example obtained in depolymerization of Nylon 6 and usually comprises caprolactam, water and oligomers.

The amount of catalyst in the initial load is 1 to 10 wt. %, 1 to 8 wt. %, preferably from 3 to 4 wt. % calculated on the mass of the initial load, and is preferably fed directly into the cyclization reactor of step (ii) by its own pipeline and dosing system before the pre-treated starting material comprising 6-aminocaproic acid from step (i) is fed into the cyclization reactor.

In continuous process this initial load is needed only at start-up, for example, not more than one or two times per year.

The cyclization reactor with the initial load is heated, at atmospheric pressure or at slightly elevated pressure, i.e. in the range from 1.0 to 1.5 bar, preferably by the action of the oil in the outer jacket and of the superheated steam. When the cyclization reactor reaches the working conditions, preferably T from about 220 to 350° C., the pre-treated starting material comprising 6-aminocaproic acid from step (i) is fed into a cyclization reactor under a controlled flow rate, in order to keep the amount of linear 6-aminocaproic acid in the cyclization reactor at low level, to avoid any side reaction. The flow rate is controlled in such a way to maintain the temperature in the cyclization reactor in the selected reaction temperature range, ideally at a constant value with the purpose to maintain also constant the kinetics of the reaction. The constant flow rate is each time defined with regard to the volume of the cyclization reactor used in the facility and should be defined in such a way that a possible temperature drop inside the cyclization reactor is minimized.

In the batch pilot trials for example, which are described below in the examples, the pre-treated solution of 6-aminocaproic acid in water was fed into the cyclization reactor in approx. 15-30 min (approximate flow rate was from 1 to 2 kg of solution per min), whereby the temperature decreased, but after additional time of 15-30 min the temperature in the cyclization reactor was recovered and kept at the selected constant value.

Nevertheless the flow rate of the pre-treated solution of 6-aminocaproic acid in water is not so critical for the reasons cited below.

If the process is performed batchwise the concentration of linear 6-aminocaproic acid in the mass inside the cyclization reactor is always decreasing until the complete conversion of 6-aminocaproic acid into caprolactam and water is achieved, preferably within the time range between 3.5-5.5 hours depending on the selected conditions inside the cyclization reactor, i.e. the temperature, the flow rate of superheated steam and the catalyst concentration.

If the process is performed continuously the flow rate of the starting material comprising 6-aminocaproic acid from step (i) into the cyclization reactor of step (ii) is preferably controlled is such a way to maintain selected steady conditions inside the cyclization reactor of step (ii), i.e. the selected temperature, the selected flow rate of superheated steam and the selected catalyst concentration are to be maintained at a constant level that means steady conditions and constant residence time according with the kinetics of the process.

Furthermore if the concentration of 6-aminocaproic acid in the reactor is too high (i.e. the flow rate of pre-treated material from step (i) into the cyclization reactor is too high), the formation of oligomers occurs (via $k_2$ reaction). This is just a temporary problem, since the constant removal of caprolactam from the reactor causes a decrease of the 6-aminocaproic acid concentration that finally shifts the equilibrium between oligomers and 6-aminocaproic acid to this last one.

Basically, if the flow rate of pre-treated material from step (i) is too high (the concentration of 6-aminocaproic acid is too high) all of it will not be converted directly to caprolactam, so some oligomers are formed. In principle there would be for some time a higher concentration of 6-aminocaproic acid inside the reactor, and the reaction to oligomers could occur. Oligomers will then be depolymerized, so in the end all 6-aminocaproic acid will be converted to caprolactam, even if in a longer time.

The macro-effect that could be observed is just a lower productivity, and one solution for a similar deviation is a temporary increase of the temperature.

Preferably the temperature of the superheated steam is in the range of 300-450° C.

Superheated steam, which is separately prepared in a pre-heater E3, enters into the cyclization reactor continuously and has a double function:
  it strips away the vapours of caprolactam and water formed in the cyclization reactor, and
  it provides, together with the heat supplied by the external thermal oil to the cyclization reactor, sufficient heat for step (iii), i.e. for the concentration of water solution of caprolactam, so no additional heating means are needed in step (iii) as will be explained hereinafter. Surprisingly, the use of superheated steam as described herein does not negatively affect the process by its potential to increase water content in the reactor.

The flow rate of the superheated steam is continuous and is maintained constant and within the range which ensures that the ratio of water to caprolactam in the vapours exiting the cyclization reactor and entering step (iii) is kept in the range of 65-35 w/w, preferably in the range of 55-45 w/w. The flow rate of the superheated steam is thus preferably in the range of 1.3-1.8 kg per kg of linear 6-aminocaproic acid which enters the cyclization reactor.

The constant continuous flow rate of the superheated steam into the reactor is important because, due to the constant flow of the superheated steam, the cyclization reactor is not a closed system and the vapours of caprolactam and water formed in the cyclization reactor are continuously striped away, thus the equilibrium in the cyclization reactor is prevented.

The reaction from 6-aminocaproic acid to caprolactam causes also the formation of a molecule of water per molecule of 6-aminocaproic acid. In the proposed process conditions, i.e. higher T and atmospheric pressure, water evaporates, so this is another factor which prevents the formation of the equilibrium in the cyclization reactor.

As already mentioned the catalyst is required to inhibit the formation of oligomers from 6-aminocaproic acid and to convert all the oligomers, that may be formed or which were present in the cyclization reactor in the initial feed, back to caprolactam, thus the complete 6-aminocaproic acid comprised in the material from step (i) is converted to caprolactam and no oligomer formation occurs in the final product.

The catalyst is present in the cyclization reactor in the amount from 1 to 10 wt. %, 1 to 8 wt. %, preferably in the amount from 3 to 4 wt. %, calculated on the total mass in the cyclization reactor.

It is desirable that the concentration of the catalyst inside the reactor is maintained at a preferred level since during the cyclization process the catalyst is partially consumed, for example by some alkaline compounds already present in the loaded material or also formed during the process or by some loss with the purge of the heavy sludge from the bottom of the cyclization reactor.

The preferred amount of the catalyst inside the cyclization reactor is maintained by the periodical addition of fresh catalyst based on the periodical analysis of the samples taken from the reactor. Ideally in a steady-state continuous process the catalyst is fed into the cyclization reactor from time to time, only when needed, i.e. when the chemical analysis indicates that the concentration of the catalyst inside the reactor is decreasing, for example has fallen below 2 wt. % calculated on the total mass in the cyclization reactor. For this reason samples of the reaction mass are taken and analysis are periodically performed. By this way it is assured that sufficient catalyst is always available for the cyclization reaction and preferably all 6-aminocaproic acid is converted to caprolactam.

Suitable catalysts are:
  phosphorous acid, poly-phosphoric acid with short chain, ammonium phosphoric acid, and in general any phosphoric salt, including metal salts, able in the process conditions to deliver the strong acid group—P—OH;
  boric acid and its salts;
  para-toluenesulphonic acid and its salts;
  phosphotungstic acid.

The preferable catalysts are:
phosphoric acid and poly-phosphoric acids with short chain
ammonium mono-, di- and tri-phosphates
sodium mono-phosphate and potassium mono-phosphate
boric acid and its mono-ammonium salt
p-toluenesulfonic acid and its mono-ammonium salt
phosphotungstic acid.

The phosphoric acid is the preferred one because it is the most efficient, easy to handle and is dosed in liquid state in a form of 30-85% water solution and is also less expensive.

From the cyclization reactor the vapour phase of caprolactam and water is led from the top of the cyclization reactor into step (iii), where condensation of the vapour phase of caprolactam and water is done. Optionally in step (iii) concentration of water solution of caprolactam is also done.

Optionally molten phase at the bottom of the cyclization reactor R2, which comprises possible residual heavies by products (for example salts, oligomers, spent catalyst), is unloaded from time to time when necessary or at the end of the process, through the bottom valve. The purge of the heavies from the bottom of the cyclization reactor is desirable particularly when the starting material comprises 6-aminocaproic acid obtained from renewable sources like bio-mass or sustainable sugars. Thus the proposed process enables also the use of bio-6ACA obtained in the bio process without the need of prior long and difficult purification steps of linear bio-6ACA and is not affected by the amount of carbohydrates content in the mixture.

In a preferred embodiment the condensation and concentration is done simultaneously in a condensation-rectification column C1, wherein an aqueous solution of epsilon caprolactam is collected at the bottom of the condensation-rectification column and low pressure steam at the top of the condensation-rectification column. Vapours of caprolactam and water coming from the step (ii) are cooled and condensed, and a liquid solution richer in caprolactam than the original vapour phase is obtained and stored into a storage vessel V1.

The condensation-rectification column can be made of any suitable material resistant to corrosion due to possible acidity at elevated temperatures used; preferably it is made of stainless steel. The number of internal stages of the condensation-rectification column necessary are defined in such a way that the separation of only water as low pressure steam with traces of caprolactam on top of the condensation-rectification column, and a liquid caprolactam solution with the concentration richer in caprolactam than in the vapour phase at the bottom of the condensation-rectification column is enabled. Preferably the concentration of caprolactam solution is in the range from 25-85 wt. %, more preferably in the range from 65-80 wt. %. The internal stages are preferably combination of standard trays and structured packing. The vapors phase is flowing up inside the column in countercurrent with the condensed liquid solution of caprolactam coming down.

The condensation-rectification column works at atmospheric pressure. In a preferred embodiment the temperature profile at the bottom of the column is maintained in a range of 115-125° C. and on the top of the column at approx. 100-102° C.

At the top of the column there is a steam condenser E1 to cool and condensate the vapours of caprolactam and water coming from the cyclization reactor of step (ii) thus recovering the high quantity of water condensation heat, which is reused in the plant facility, for example for heating the water to handle caprolactam as a pumpable liquid or for example for concentrating the starting material in a form of a solution to contain at least 50 wt. % of 6-aminocaproic acid on the total mass of the starting material.

At the bottom of the condensation-rectification column no heating means are required, the heat necessary for the concentration is supplied from the vapours in the step (ii), so a significant energy saving is possible.

The final product coming out from step (iii) is a water solution of raw caprolactam, with the properties which correspond to the properties and quality of raw epsilon caprolactam obtained by traditional way (i.e. by the reaction known as the "Beckmann rearrangement") before its final purification.

In a preferred embodiment the starting material comprises 6-aminocaproic acid in a form of a solution in water with the concentration of 6-aminocaproic acid at least 50 wt. %, based on the total mass of the starting material.

As already mentioned said 6-aminocaproic acid can be obtained either from traditional petro chemical processes or can be obtained from biochemical processes, wherein higher amounts of carbohydrates and other contaminants coming from fermentation during the production of the bio-based 6-ACA are comprised in the 6-aminocaproic acid. With the proposed process the 6-aminocaproic acid starting material can optionally comprise at least 12.5 wt. %, 10 wt. %, 5 wt. %, 4 wt. %, 3.5 wt. %, 3.4 wt. %, 3 wt. %, 2 wt. % or 1 wt. % and up to 15 wt. %, 12.5 wt. %, 10 wt. %, 5 wt. % or 4 wt. % of carbohydrate, based on the mass of the 6-aminocaproic acid, thus a process for preparing carbohydrate-derived epsilon caprolactam is an advantage of the present disclosure. In bio-6ACA some possible residual carbohydrates, i.e. sugars like monosaccharide glucose, fructose and disaccharide maltose, isomaltose and/or sucrose are present in the starting material.

Said process comprises cyclising a mixture comprising 6-aminocaproic acid and carbohydrate in the presence of superheated steam and an acid catalyst in a cyclization reactor under conditions to provide continuous and complete conversion to epsilon caprolactam, optionally whereby the 6-aminocaproic acid is converted at equal to or greater than 95%, 96%, 97%, 98%, 99%, 99.5%, 99.9% or 100% to epsilon caprolactam, thereby forming vapors of epsilon caprolactam and water. The acid catalyst is in the amount of at least 2 wt. %, calculated on the total mass in the cyclization reactor, preferably in the amount from 3 to 4 wt. %. Suitable catalysts are: phosphorous acid, poly-phosphoric acid with short chain, ammonium phosphoric acid, and in general any phosphoric salt, including metal salts, able in the process conditions to deliver the strong acid group—P—OH; boric acid and its salts; para-toluenesulphonic acid and its salts; and phosphotungstic acid. The preferable catalysts are: phosphoric acid and poly-phosphoric acids with short chain; ammonium mono-, di- and tri-phosphates; sodium mono-phosphate and potassium mono-phosphate; boric acid and its mono-ammonium salt; p-toluenesulfonic acid and its mono-ammonium salt; and phosphotungstic acid. The phosphoric acid is the most preferred because it is the most efficient, easy to handle and is dosed in liquid state in a form of 30-85% water solution and is also less expensive. The cyclization reactor works at atmospheric pressure or at slightly elevated pressure, i.e. in the range from 1.0 to 1.5 bar, and at temperature in the range from 220 to 350°. The superheated steam has a temperature in the range of 300-450° C. and the flow rate of the superheated steam is within the range which ensures that the ratio of water to caprolactam in the vapours exiting the cyclization reactor is kept in the range of 65-35 w/w, preferably 55-45 w/w. Conditions for the above steps are also as described throughout this application.

Said process may additionally comprise pre-treatment of the mixture comprising 6-aminocaproic acid and carbohydrate as described in step (i) above. In step (i) said mixture is preheated to the temperature in or near the temperature of a cyclization reactor to accelerate a cyclization reaction. Conditions for the above steps are also as described throughout this application.

Optionally the cyclization reactor is for the start up phase brought at a pressure and temperature favouring cyclization and steam-stripping, by feeding the cyclization reactor with an initial load of a caprolactam solution and a catalyst, prior the pre-heated mixture from step (i) is fed into the cyclization reactor. Conditions for the above steps are also as described throughout this application.

Said process additionally comprises condensation of the vapour mixture comprising epsilon caprolactam and water obtained in the cyclization reactor and further concentration of the aqueous solution of epsilon caprolactam, whereby condensation and concentration is done simultaneously in a condensation-rectification column as described in step (iii) above, wherein an aqueous solution of epsilon caprolactam with the concentration richer in caprolactam than in the vapour phase is collected at the bottom of the condensation-rectification column and low pressure steam at the top of the condensation-rectification column. Conditions for the above steps are also as described throughout this application.

The features of the process according to the disclosure and the advantages thereof will now be demonstrated further with the examples so as to enable improved comprehension of the process itself. These examples are not to be considered limiting in terms of the type and amount of compounds used, operational parameter ranges, etc.

EXAMPLES

Example 1 (One Step Process in a Closed System at Elevated T and Elevated Pressure with No Catalyst: Standard Process, Reference for the Innovative Process)

The following materials are introduced in a pilot reactor made of stainless steel, having a volumetric capacity of 170 liters and provided with an outer jacket (unit R1a):

6-ACA, powder: 12.5 kg (80% by weight on the total mass);

water: 3.125 kg (20% by weight on the total mass).

The reactor is then heated adiabatically, starting from room temperature and atmospheric pressure, to reach the following conditions, i. e. maintenance conditions:

pressure: 8.5 bar;

liquid temperature: 193° C.;

vapor temperature: 204° C.

After a maintenance time of 30 minutes, the heater is turned off, so the temperature decreases and with it the pressure too.

Once the temperature decreased below 100° C. the reactor was opened. The obtained solid "white" material was analyzed (i.e.: quantitative gas chromatography, dry matter, titration of end groups)

Based on the analysis on the sample the composition found was the following one:

| caprolactam: | 0.0 kg | 0.0 wt. % |
| 6-ACA: | 4.1 kg | 26.2 wt. %; |
| oligomers: | 7.25 kg | 46.6 wt. %; |
| water: | 4.25 kg | approx. 27.2 wt. %. |

The conversion of 6-ACA is not complete and no caprolactam is formed:

6-ACA conversion: 67.4%;

6-ACA to CPL yield: 0%.

The experiment demonstrates that based only on high temperature and relatively high pressure no caprolactam is formed, while 6-ACA is partially converted to oligomers. The conversion to oligomers was delivering 1 mole of H2O per mole of 6-ACA, so in the closed system adopted for the trial of said example the original amount of water was increased with the one coming from the reaction.

Example 2a (Three Step Process, without Catalyst)

Step (i).

The following materials are introduced in a pilot reactor made of stainless steel, having a volumetric capacity of 170 liters and provided with an outer jacket (unit R1a):

6-ACA, powder: 25 kg (80% by weight on the total mass);

water: 6.25 kg (20% by weight on the total mass).

The reactor is then heated adiabatically, starting from room temperature and atmospheric pressure, to reach the following conditions, i.e. maintenance conditions:

pressure: 8.2 bar;

liquid temperature: 190° C.;

vapor temperature: 203° C.

The mixture was kept on these conditions for a maintenance time of 30 minutes, and then all the material was transferred to a cyclization reactor in step (ii).

During the maintenance time 6-ACA is completed dissolved in the water, the vapors formed from the liquid water loaded at the beginning created in the mean time an inert atmosphere avoiding the thermal degradation of 6-ACA and even if some part of the linear substance, i.e. 6-ACA, was transformed in oligomers like demonstrated in the example 1, the total mixture is in a liquid state at a temperature close to the one necessary to realize the cyclization reaction of step (ii), while the water is in condition to flash immediately when entering cyclization rector in step (ii).

Step (ii).

The cyclization reactor R2 made of stainless steel, having a volumetric capacity of 190 liters and an outer jacket for thermal oil circulation was prepared and brought to the working conditions. The stirring inside the reactor is guaranteed by the continuous feeding of the overheated steam through the distributor located at the bottom of the reactor R2. The reactor R2 was loaded with the initial feed of caprolactam solution composed of caprolactam, oligomers and water (see Table 1 which presents schematic mass balance calculation at the end of Example 2a).

The reactor R2 was heated to T=238° C., at atmospheric pressure, by the action of the oil in the outer jacket and of the overheated steam (in this example the main supply of heat is the thermal oil).

The mixture form step (i) is fed into the cyclization reactor R2.

The flash of the water causes a short initial temperature decrease down to 184° C., followed by the increase up to 254° C. due to the heating, while the overheated steam is continuously fed at a constant rate of 40 l/h into the cyclization reactor.

The 6-ACA then undergoes the cyclization reaction, with the production of CPL; the polymerization to oligomers can occur as a side reaction. As soon as the CPL is formed it is stripped away by the overheated steam to step (iii).

Step (iii).

The vapors as a mixture of water steam and caprolactam coming from the cyclization reaction of 6-ACA are continuously sent to a rectification column C1. In the pilot unit the rectification column is packed bed rectification column made of stainless steel, with a condenser (without any recovery of the heat in the pilot unit) and without a boiler as the heat for rectification is recovered from the energy delivered in the previous step (ii).

As cooling and condensation medium some liquid water is fed to the upper part of the rectification column.

From the top of the rectification column C1 the water steam at T 100-102° C. practically without any caprolactam is sent to condensate in a separate condenser E1, while from the bottom of the rectification column a concentrate caprolactam water solution at T 110-115° C. is collected and stored into a storage vessel V1.

In the pilot unit the rectification-condensation column, originally built for several normal research activities, in the vapors some small amount of caprolactam is present, as the internal bed is made up using some simple traditional Raschig rings.

The oligomers remained are unloaded from the bottom of the cyclization reactor R2 at the end of the trial.

The total balance, considering the difference between the inputs and the outputs, is the following:

caprolactam: +3.7 kg;
oligomers: +17.9 kg;
6-ACA: −25 kg (equivalent to 21.6 kg of caprolactam)

From the mass balance the following parameters are calculated:

6-ACA conversion: 100%;
6-ACA to CPL yield: 17.1%;
Oligomers: 82.9%.

The quality of the final raw CPL is similar to the quality of the traditional raw caprolactam.

In particular:

GC purity (% area): 99.4%;
GC peaks: 12 (CPL+7 lights and 4 heavies).
Visual aspect: CPL solution color transparent In Table 1 the schematic mass balance calculation at the end of Example 2a is presented. The original 6ACA is losing H2O in both cases, to become CPL or oligomers, for this reason the 25 kg of 6ACA in the feed become 21.6 kg.

TABLE 1

| Example 2a | R1, initial load kg | % | R2 preparation kg | % | Catalyst 75% kg | CPL solution top C1 % | kg | CPL solution in V1 % | kg | Bottom R2 kg | Total dry "IN" | Total dry "OUT" | Delta OUT-IN |
|---|---|---|---|---|---|---|---|---|---|---|---|---|---|
| Caprolactam | 0 | 0.0 | 57.6 | 72.0 | | 1.50 | 3.00 | 25.3 | 58.30 | | 57.6 | 61.3 | 3.7 |
| 6-ACA | 25 | 80.0 | 0 | 0.0 | | | | | | | 21.6 | 0 | |
| Oligomers | 0 | 0.0 | 6.4 | 8.0 | | | | | | | 6.4 | 24.3 | 17.9 |
| Water | 6.25 | 20.0 | 16 | 20.0 | 0 | | | | | | | | |
| H₃PO₄ | | | | | 0 | | | | | | | | |
| Final Sludges from R2 | | | | | | | | | | | | | |
| Oligomers | | | | | | | | | | 24.3 | | | |
| H₃PO₄ | | | | | | | | | | 0 | | 0 | |
| Heavy Byproduct/Salts | | | | | | | | | Traces=> | 0 | | 0 | |
| Total | 31.25 | 100 | 80 | 100 | 0 | 0.015 | 200 | | 230 | 24.3 | 85.6 | 85.6 | 21.6 |

Yield to CPL: 17.2%
Yield to oligomers: 83.0%
6ACA Conversion: 100%

Example 2b (Three Step Process, without Catalyst but with Sugars Simulating the Bio Based 6-ACA with its Residual Original Raw Materials)

The substance 6-ACA to convert to the cyclic monomer caprolactam can be produced from petro raw material source or from renewable source, i.e. from a culture medium comprising biomass, wherein the culture medium comprises one or more carbohydrates like sugars first and/or second generation type, in this application referred as bio-6ACA. In bio-6ACA some possible residual carbohydrates, i.e. sugars like monosaccharide glucose, fructose and disaccharide maltose, isomaltose and/or sucrose are present in the starting material. The three steps process without the use of catalyst was tested to simulate the influence of residual sugar contamination present in 6-ACA on the yield and the quality of the produced caprolactam.

Step (i).

The following materials are introduced in a pilot reactor made of stainless steel, having a volumetric capacity of 170 liters and provided with an outer jacket (R1a):

6-ACA, powder: 25 kg (80% by weight on the total mass);
Sugar mix: 0.85 kg (equivalent to 3.4% by weight on dry 6-ACA)
water: 6.25 kg (20% by weight on the total mass, not counting the sugar mix).

Remark on sugar mix: the selected mixture was:

Glucose 0.05 kg
Fructose 0.175 kg
Maltose 0.625 kg

The mixture is selected to simulate the usual fermentation process considering that the glucose and fructose are the starting renewable monosaccharide raw materials and the maltose can be a disaccharide derived as byproduct during the process of producing bio-6ACA. The residual sugars after fermentation and purification process usually should be in the order of 0.3 wt. % (referred to the total fermentation broth) while for checking the suitability of the process, a 3 times more concentrated mixture was used.

The reactor R1a is then heated adiabatically, starting from room temperature and atmospheric pressure, to reach the following conditions, i.e. maintenance conditions:
pressure: 8.2 bar;
liquid temperature: 188° C.;
vapor temperature: 206° C.

The mixture was kept on these conditions for a maintenance time of 30 minutes, and then all the material was transferred to a cyclization reactor in step (ii).

During the maintenance time 6-ACA is completed dissolved in the mixture, the vapors formed from the liquid water loaded at beginning created in the mean time an inert atmosphere avoiding the thermal degradation and even if some part of the linear substance was transformed to oligomers like seen by example 1, the total mixture was in liquid state at a temperature closed to the one necessary to realize the cyclization reaction of step (ii), while the water is in condition to flash immediately.

Step (ii).

The cyclization reactor (R2) made of stainless steel, having a volumetric capacity of 190 liters and an outer jacket for thermal oil circulation was prepared and brought to the working conditions. The stirring inside the reactor is enabled as explained in example 2a. The reactor was fed with the initial load of caprolactam solution composed of caprolactam, oligomers and water (see Table 2 which presents schematic mass balance calculation at the end of Example 2b).

The reactor was heated to T=257° C., at atmospheric pressure, by the action of the oil in the outer jacket and of the superheated steam (in this example the main supply of heat is the thermal oil).

The mixture form step (i) is fed into the cyclization reactor.

The flash of the water causes a short initial temperature decrease down to 205° C., followed by the increase up to 262° C. due to the heating, while the superheated steam is continuously fed at constant rate of 40 l/h to the cyclization reactor.

The 6-ACA then undergoes the cyclization reaction, with the production of CPL; the polymerization to oligomers can occur as a side reaction. As soon as the CPL is formed it is stripped away by the superheated steam to step (iii).

Step (iii).

The vapors as mixture of water steam and caprolactam coming from the cyclization reaction of 6-ACA are continuously sent to a packed bed column made of stainless steel (C1), with condenser (without any recovery of the heat in the pilot unit) and without boiler as there the heat for rectification is recovered from the energy delivered in the previous step (ii). As cooling and condensation medium some liquid water is fed to the high part of the column.

From the top of the column the water steam at 100-102° C. without practically any caprolactam is sent to condensate in a separate condenser, while from the bottom of the column a caprolactam water solution richer in caprolactam as in vapour phase coming from the cyclization reactor at 110-115° C. is collected and stored into a storage vessel.

In the pilot unit the rectification-condensation column is the same as described in example 2a.

The oligomers remained are unloaded from the bottom of the cyclization reactor at the end of the trial.

The total balance, considering the difference between the inputs and the outputs, is the following:
caprolactam: +4.4 kg;
oligomers: +17.2 kg;
6-ACA: −25 kg (equivalent to 21.6 kg of caprolactam).

From the mass balance the following parameters are calculated:
6-ACA conversion: 100%;
6-ACA to CPL yield: 20.4%;
Oligomers: 79.7%.

The quality of the final raw CPL is similar to the quality of the traditional raw caprolactam.
In particular:
GC purity (% area): 98.7%;
GC peaks: 11 (CPL+7 lights and 3 heavies).
Visual aspect: CPL solution color dark yellow The experiment shows that with the three step process without any use of catalyst the conversion of 6-ACA, the yield to Caprolactam and the quality of the monomer is not at all affected by the original raw materials like sugars and the results were practically the same obtained with the petro linear 6-ACA alone (see example 2a). See Table 2.

TABLE 2

| Example 2b | R1, initial load | | R2 preparation | | Catalyst 75% | CPL solution top C1 | | CPL solution in V1 | | Bottom R2 | Total dry "IN" | Total dry "OUT" | Delta OUT-IN |
|---|---|---|---|---|---|---|---|---|---|---|---|---|---|
| | kg | % | kg | % | kg | % | kg | % | kg | kg | | | |
| Caprolactam | 0 | 0.0 | 57.6 | 72.0 | | 1.50 | 3.00 | 25.7 | 59.00 | | 57.6 | 62 | 4.4 |
| 6-ACA | 25 | 77.9 | 0 | 0.0 | | | | | | | 21.6 | 0 | |
| Oligomers | 0 | 0.0 | 6.4 | 8.0 | | | | | | | 6.4 | 23.600 | 17.2 |
| Water | 6.25 | 19.5 | 16 | 20.0 | 0 | | | | | | | | |
| Glucose | 0.050 | 0.2 | | | | | | | | | | | |
| Fructose | 0.175 | 0.5 | | | | | | | | | | | |
| Maltose | 0.625 | 1.9 | | | | | | | | | | | |

TABLE 2-continued

| Example 2b | R1, initial load kg | % | R2 preparation kg | % | Catalyst 75% kg | % | CPL solution top C1 kg | % | CPL solution in V1 kg | Bottom R2 kg | Total dry "IN" | Total dry "OUT" | Delta OUT-IN |
|---|---|---|---|---|---|---|---|---|---|---|---|---|---|
| $H_3PO_4$ | | | | | 0 | | | | | | | | |
| Final Sludges from R2 | | | | | | | | | | | | | |
| Oligomers | | | | | | | | | | 23.6 | | | |
| $H_3PO_4$ | | | | | | | | | | 0 | | 0 | |
| Heavy Byproduct/Salts | | | | | | | | | | 0 | | 0.000 | |
| Total | 32.1 | 100 | 80 | 100 | 0 | | 0.015 | 200 | | 230 | 23.6 | 85.6 | 85.6 | 21.6 |

Yield to CPL: 20.4%
Yield to oligomers: 79.8%
6ACA Conversion: 100%
The total amount of sugar is equivalent to 0.85/25=>3.4 wt. % based on the mass of the 6-aminocaproic acid.

Example 3 (Three Step Process with Catalyst 1.33 wt. % Based on the Total Mass in the Cyclization Reactor)

Step (i).
The following materials are introduced in a pilot reactor made of stainless steel, having a volumetric capacity of 170 liters and provided with outer jacket (unit R1):
6ACA, powder: 25 kg (80% by weight on the total mass);
water: 6.25 kg (20% by weight on the total mass).
The reactor is then heated adiabatically, starting from room temperature and atmospheric pressure, to reach the following conditions i. e. maintenance conditions:
pressure: 8.2 bar;
liquid temperature: 191° C.;
vapour temperature: 198° C.
The mixture was kept on these conditions for a maintenance time of 30 minutes, and then all the material was transferred to a cyclization reactor in step (ii) in the same manner and with the same effects explained in the previous example 2a.

Step (ii).
The cyclization reactor R2 made of stainless steel, having a volumetric capacity of 190 liters and an outer jacket for thermal oil circulation was prepared and brought to the working conditions. The stirring inside the reactor is guaranteed by the continuous feeding of the superheated steam through the special distributor located at the bottom. Reactor was fed with the initial load of caprolactam solution composed of caprolactam, oligomers and water and with phosphoric acid in the amount of 1.33 wt. %, based on the total mass in the cyclization reactor (see Table 3 which presents schematic mass balance calculation at the end of Example 3).
The liquid catalyst H3PO4 with concentration of 75% in water is fed into the cyclization reactor from time to time (when the chemical analysis indicated that the concentration of the catalyst inside the reactor fell below 2 wt. %), to guarantee its presence in the reacting mixture all the time during the trial.
The reactor was heated to T=263° C., at atmospheric pressure, by the action of the oil in the outer jacket and of the superheated steam (in this example the main supply of heat is the thermal oil).

The mixture form step (i) is fed into the cyclization reactor.
The flash of the water causes a short initial temperature decrease down to 190° C., followed by the increase given by the heating up to 266° C., while the superheated steam is continuously fed at constant rate of 40 l/h to the reactor.
The 6ACA then undergoes the cyclization reaction, with the production of CPL; the polymerization to oligomers can occur as a side reaction. As soon as the CPL is formed it is stripped away by the overheated steam to step (iii).

Step (iii).
The vapors as mixture of water steam and caprolactam coming from the cyclization reaction of 6ACA are continuously sent to a packed bed column made of stainless steel (Unit C1), with condenser (without any recovery of the heat in the pilot unit) and without boiler as there the heat for rectification is recovered from the energy delivered in the previous step (ii). As cooling and condensation medium some liquid water is fed to the high part of the column.
From the top of the column the water steam at 100-102° C. without practically any caprolactam is sent to condensate in a separate condenser, from the bottom of the column a concentrate caprolactam water solution at 110-115° C. is collected and stored into a storage vessel.
In the pilot unit the rectification-condensation column is the same as described in example 2a.
The oligomers remained are unloaded from the bottom of the cyclization reactor at the end of the trial.
The total balance, considering the difference between the inputs and the outputs, is the following:
caprolactam: +15.0 kg;
oligomers: +6.6 kg
6ACA: −25 kg (equivalent to 21.6 kg of caprolactam).
From the mass balance the following parameters are calculated:
6ACA conversion: 100%;
6ACA to CPL yield: 69.4%.
Oligomers: 30.6%
The quality of the final raw CPL is similar to the quality of the traditional raw caprolactam.
In particular:
GC purity (% area): 99.3%;
GC peaks: 10 (CPL+5 lights and 4 heavies);
Visual aspect: CPL solution color transparent

TABLE 3

| Example 3 | R1, initial load | | R2 preparation | | Catalyst 75% | CPL solution top C1 | | CPL solution in V1 | | Bottom R2 | Total dry "IN" | Total dry "OUT" | Delta OUT-IN |
|---|---|---|---|---|---|---|---|---|---|---|---|---|---|
| | kg | % | kg | % | kg | % | kg | % | kg | kg | | | |
| Caprolactam | 0 | 0.0 | 57.6 | 72.0 | | 1.50 | 3.00 | 30.3% | 69.60 | | 57.6 | 72.6 | 15 |
| 6-ACA | 25 | 80.0 | 0 | 0.0 | | | | | | | 21.6 | 0 | |
| Oligomers | 0 | 0.0 | 6.4 | 8.0 | | | | | | | 6.4 | 11.77 | 6.55 |
| Water | 6.25 | 20.0 | 16 | 20.0 | 0.4 | | | | | | | | |
| H3PO4 | | | | | 1.18 | | | | | | | | |
| Final Sludges from R2 | | | | | 1.33 | | | | | | | | |
| Oligomers | | | | | | | | | | 12.95 | | | |
| H3PO4 | | | | | | | | | | 1.18 | | 1.18 | |
| Heavy Byproduct/Salts | | | | | | | | Traces=> | | 0 | | 0 | |
| Total | 31.25 | 100 | 80 | 100 | 1.59 | 0.015 | 200 | | 230 | 14.13 | 85.6 | 85.55 | 21.55 |

Yield to CPL: 69.6%
Yield to oligomers: 30.4%
6ACA Conversion: 100%

Example 4 (Three Step Process, with Catalyst 4.0 wt. % on the Total Mass in the Cyclization Reactor)

Step (i).

The following materials are introduced in a pilot reactor made of stainless steel, having a volumetric capacity of 170 liters and provided with outer jacket (unit R1):

6ACA, powder: 25 kg (80% by weight on the total mass); water: 6.25 kg (20% by weight on the total mass).

The reactor is then heated adiabatically, starting from room temperature and atmospheric pressure, to reach the following conditions, i.e. maintenance conditions:

pressure: 8.3 bar;
liquid temperature: 185° C.;
vapor temperature: 189° C.

The mixture was kept on these conditions for a maintenance time of 30 minutes, and then all the material was transferred to a cyclization reactor in step (ii) in the same manner and with the same effects explained in the previous example 2a.

Step (ii).

The cyclization reactor R2 made of stainless steel, having a volumetric capacity of 190 liters and an outer jacket for thermal oil circulation was prepared and brought to the working conditions. The stirring inside the reactor is guaranteed by the continuous feeding of the superheated steam through the special distributor located at the bottom. The reactor was fed with the initial load of caprolactam solution composed of caprolactam, oligomers and water and with phosphoric acid in the amount of 4.0 wt. % based on the total mass in the cyclization reactor (see Table 4 which presents schematic mass balance calculation at the end of Example 4).

The liquid catalyst H3PO4 with concentration of 75% in water was is fed into the cyclization reactor from time to time (when the chemical analysis indicated that the concentration of the catalyst inside the reactor fell below 2 wt. %), to guarantee its presence in the reacting mixture all the time during the trial.

The reactor was heated to T=266° C., at atmospheric pressure, by the action of the oil in the outer jacket and of the superheated steam (in this example the main supply of heat is the thermal oil).

The mixture form step (i) is fed into the cyclization reactor.

The flash of the water causes a short initial temperature decrease down to 208° C., followed by the increase given by the heating up to 268° C., while the overheated steam is continuously fed at constant rate of 40 l/h to the reactor.

The 6ACA then undergoes the cyclization reaction, with the production of CPL; the polymerization to oligomers can occur as a side reaction. As soon as the CPL is formed it is stripped away by the superheated steam to step (iii).

Step (iii).

The vapors as mixture of water steam and caprolactam coming from the cyclization reaction of 6ACA are continuously sent to a packed bed rectification column C1 made of stainless steel, with condenser (without any recovery of the heat in the pilot unit) and without boiler as there the heat for rectification is recovered from the energy delivered in the previous step. As cooling and condensation medium some liquid water is fed to the high part of the column.

From the top of the column the water steam at 100-102° C. practically without any caprolactam is sent to condensate in a condenser, from the bottom of the column a concentrate caprolactam water solution at 110-115° C. is collected and stored into a storage vessel.

In the pilot unit the rectification-condensation column is the same as described in example 2a.

The oligomers remained are unloaded from the bottom of the cyclization reactor at the end of the trial.

The total balance, considering the difference between the inputs and the outputs, is the following:

caprolactam: +24.8 kg;
oligomers: −3.2 kg
6ACA: −25 kg (equivalent to 21.6 kg of caprolactam).

From the mass balance the following parameters are calculated:

6ACA conversion: 100%;
6ACA to CPL yield: 100%.
Oligomers: 0%

The quality of the final raw CPL is similar to those of the traditional raw caprolactam. In particular:

GC purity (% area): 99.8%;
GC peaks: 8 (CPL+6 lights and 1 heavies);
Visual aspect: CPL solution transparent

TABLE 4

| Example 4 | R1, initial load kg | R1, initial load % | R2 preparation kg | R2 preparation % | Catalyst 75% kg | CPL solution top C1 % | CPL solution top C1 kg | CPL solution in V1 % | CPL solution in V1 kg | Bottom R2 kg | Total dry "IN" | Total dry "OUT" | Delta OUT-IN |
|---|---|---|---|---|---|---|---|---|---|---|---|---|---|
| Caprolactam | 0 | 0.0 | 57.6 | 72.0 | | 1.50 | 3.00 | 34.5% | 79.40 | | 57.6 | 82.4 | 24.8 |
| 6-ACA | 25 | 80.0 | 0 | 0.0 | | | | | | | 21.6 | 0 | |
| Oligomers | 0 | 0.0 | 6.4 | 8.0 | | | | | | | 6.4 | −0.35 | −3.2 |
| Water | 6.25 | 20.0 | 16 | 20.0 | 1.16 | | | | | | | | |
| H3PO4 | | | | | 3.55 | | | | | | | | |
| Final Sludges from R2 | | | | | 3.99 | | | | | | | | |
| Oligomers | | | | | | | | | | 3.2 | | | |
| H3PO4 | | | | | | | | | | 3.55 | | 3.55 | |
| Heavy Byproduct/Salts | | | | | | | | Traces=> | | 0 | | 0 | |
| Total | 31.25 | 100 | 80 | 100 | 4.75 | 0.015 | 200 | | 230 | 6.75 | 85.6 | 85.6 | 21.6 |

Yield to CPL: 114.8%
Yield to oligomers: −14.8%
6ACA Conversion: 100%
Net yield on 6—ACA: 100%

Examples 5-9

Following the same procedure as used in the Example 4, using the same amount of materials and the amount of catalyst was 4 wt. % based on the total mass of the initial load, some trials were repeated and conducted at different temperature to evaluate the impact on the total time necessary for the complete conversion of the 6ACA to transform in the equivalent caprolactam. Results are presented in Table 5.

TABLE 5

| Example | 6ACA to CPL yield [%] | Average temperature [° C.] | Reaction time [h:min] | GC purity [%] | GC light peaks- GC heavy peaks |
|---|---|---|---|---|---|
| Ex 5 | 100 | 248 | 06:15 | 99.3 | 6-2 |
| Ex 6 | 100 | 252 | 05:40 | 99.7 | 2-1 |
| Ex 7 | 100 | 253 | 04:40 | 98.9 | 7-4 |
| Ex 8 | 100 | 256 | 04:10 | 99.5 | 5-2 |
| Ex 9 | 100 | 261 | 03:45 | 99.8 | 6-1 |

For each trial the total distribution of the inlet and outlet mass was the same or similar as indicated in the mass balance of Example 4.

Examples 10-11

As already described in the example 2b, the substance 6-ACA can be produced from petro raw material source or from renewable source i.e. from a culture medium comprising biomass, wherein the culture medium comprises one or more carbohydrates like sugars first and/or second generation type, in this application referred as bio-6ACA. In bio-6ACA some possible residual carbohydrates like monosaccharide glucose, fructose and disaccharide maltose, isomaltose and/or sucrose are present in the starting material.

The process of the disclosure (with the use of catalyst) was tested to simulate the influence of residual sugar contamination present in bio-6ACA on the yield and the quality of the produced caprolactam.

For this purpose the following mixture of sugars in step (i) of the process was added to 6-ACA:
glucose: 0.02 wt. % Ex 10; 0.2 wt. % Ex 11a and 0.6 wt. % Ex 11 b, based on 6-ACA;
fructose: 0.07 wt. % Ex 10; 0.7 wt. % Ex 11a and 2.1 wt. % Ex 11 b, based on 6-ACA;
maltose: 0.25 wt. % Ex 10; 2.5 wt. % Ex 11a and 7.5 wt. % Ex 11 b, based on 6-ACA;
which is equivalent to:
total sugars 0.34 wt. % in case of Example 10;
total sugars 3.4 wt. % in case of Example 11a;
total sugars 10.2 wt. % in case of Example 11 b.

The trials with the above sugars as contaminants were performed with the same procedure as used in the Example 4 to evaluate conversion and yield of the 6-ACA to equivalent caprolactam in the process of the disclosure. At same time the quality of the raw caprolactam was checked. Results are presented in Table 6.

TABLE 6

| | | | Example | | | |
|---|---|---|---|---|---|---|
| | | | Ex. 8 Ref. | Ex. 10 | Ex. 11a | Ex. 11b |
| Load in Step (i) | 6ACA | [kg] | 25 | 25 | 25 | 25 |
| | H2O | [kg] | 6.25 | 6.25 | 6.25 | 6.25 |
| | Total sugars | [% on 6ACA] | 0 | 0.34 | 3.4 | 10.2 |
| Load in Step (ii) | Caprolactam | [kg] | 57.6 | 57.6 | 57.6 | 57.6 |
| | Oligomers | [kg] | 6.4 | 6.4 | 6.4 | 6.4 |
| | Catalyst H3PO4 on | % | 4 | 4 | 4 | 4 |

TABLE 6-continued

|  |  |  | Example | | | |
|---|---|---|---|---|---|---|
|  |  |  | Ex. 8 Ref. | Ex. 10 | Ex. 11a | Ex. 11b |
| Output mass | Caprolactam | [kg] | +22.8 | +23.5 | +23.9 | +22.3 |
|  | Oligomers | [kg] | −1.2 | −2.5 | −2.3 | −0.7 |
|  | 6ACA | [kg] | −25 | −25 | −25 | −25 |
| Results | 6ACAtoCPLyield | [%] | 100 | 100 | 100 | 100 |
|  | Average T in Step 2 | [° C.] | 256 | 257 | 251 | 255 |
|  | Reaction Time | [h:min] | 04:10 | 04:15 | 04:30 | 04:35 |

For each trial the total distribution of the inlet and outlet mass was the same or similar as indicated in the mass balance of Example 4, with the mixture of total sugars loaded in the reactor R1 of step 1.

The caprolactam produced in each trial was collected in a vessel and analyzed via gas chromatography.

The results are presented in table 7.

TABLE 7

|  | Example | | | |
|---|---|---|---|---|
|  | Ex 8 Ref | Ex 10 | Ex 11a | Ex 11b |
| Sugars amount | — | 0.34% | 3.4% | 10.2% |
| CPL color | transparent | light yellow | dark yellow | dark brown |
| GC purity | 99.5% | 99.1% | 99.4% | 98.7% |
| Peaks of lights | 5 | 7 | 9 | 12 |
| Peaks of heavies | 2 | 4 | 2 | 3 |
| Total number of peaks | 7 | 11 | 11 | 15 |

As can be concluded from the presented results the conversion and yield of 6ACA to caprolactam did not suffer negative impacts in the process of the disclosure and also the quality of caprolactam remained at usual level: the yellowish color at higher concentration of contaminants can suggest the presence of few ppm of byproducts coming from sugars.

Examples 12-15

The substance 6-ACA to convert to the cyclic monomer caprolactam produced from renewable source like sugars first and/or second generation type, need in the fermentation process some salts as nutrients, inorganic and also organic salts being these last ones also generated directly during the bio-process.

The process of the disclosure was tested also with a combination of these additional potential contaminants of the bio-6ACA. For this purpose the following mixture of salts was added to 6-ACA in the step (i) of the process as indicated in the table 8.

TABLE 8

| % of the salts on the dry 6-ACA for each trial | | | | |
|---|---|---|---|---|
| Salts | Ex 12 | Ex 13 | Ex14 | Ex15 |
| Ammonium sulfate | 0.38% | 1.14% |  |  |
| Ammonium phosphate | 0.44% | 1.32% |  |  |
| Potassium phosphate | 0.66% | 1.98% |  |  |
| Sodium sulfate | 0.12% | 0.36% |  |  |
| Magnesium Sulfate | 0.07% | 0.21% |  |  |
| Ammonium acetate |  |  | 1.48% | 4.44% |
| Ammonium formiate |  |  | 0.20% | 0.60% |
| Sodium lactate sol. 60% |  |  | 0.34% | 1.02% |
| Citric acid•1H2O |  |  | 0.58% | 1.74% |
| Sodium succinate 6H2O |  |  | 0.64% | 1.92% |
| Total % on dry 6-ACA | 1.67% | 5.01% | 3.24% | 9.72% |
| Total dosage ratio | 1 | 3 | 1 | 3 |

The trials with the inorganic and organic salts as contaminants were performed with the same procedure as used in the Example 4 to evaluate conversion and yield of the 6-ACA to equivalent caprolactam in the process of the disclosure. At same time the quality of the raw caprolactam was checked.

The results are presented in table 9.

TABLE 9

| Trials with salts: | | | | | | | |
|---|---|---|---|---|---|---|---|
|  |  |  | Example | | | | |
|  |  |  | Ex. 8 Ref. | Ex. 12 | Ex. 13 | Ex. 14 | Ex. 15 |
| Load in Step (i) | 6ACA | [kg] | 25 | 25 | 25 | 25 | 25 |
|  | H2O | [kg] | 6.25 | 6.25 | 6.25 | 6.25 | 6.25 |
|  | Total inorganic salts | [% on 6ACA] | 0 | 1.67% | 5.01% | 0 | 0 |
|  | Total organic salts | [% on 6ACA] | 0 | 0 | 0 | 3.24% | 9.72% |
| Load in Step (ii) | Caprolactam | [kg] | 57.6 | 57.6 | 57.6 | 57.6 | 57.6 |
|  | Oligomers | [kg] | 6.4 | 6.4 | 6.4 | 6.4 | 6.4 |
|  | Catalyst H3PO4 on total | % | 4 | 4 | 4 | 4 | 4 |

TABLE 9-continued

Trials with salts:

| | | | Example | | | | |
|---|---|---|---|---|---|---|---|
| | | | Ex. 8 Ref. | Ex. 12 | Ex. 13 | Ex. 14 | Ex. 15 |
| Output mass | Caprolactam | [kg] | +22.8 | +26.4 | +26.9 | +25.3 | +19.7 |
| | Oligomers | [kg] | −1.2 | −4.8 | −5.3 | −3.7 | +1.9 |
| | 6ACA | [kg] | −25 | −25 | −25 | −25 | −25 |
| Results | 6ACAtoCPLyield | [%] | 100 | 100 | 100 | 100 | 91.2 |
| | Average T in Step (ii) | [° C.] | 256 | 256 | 260 | 261 | 251 |
| | Reaction Time | [h:min] | 04:10 | 4:40 | 4:40 | 4:50 | 4:15 |

For each trial the total distribution of the inlet and outlet mass was the same or similar as indicated in the mass balance of Example 4, with the mixture of total salts loaded in the reactor R1 of step (i).

The caprolactam produced in each trial was collected in a vessel and analyzed via gas chromatography.

The results are presented in the table 10.

TABLE 10

| | Example | | | | |
|---|---|---|---|---|---|
| | Ex 8 Ref | Ex 12 | Ex 13 | Ex 14 | Ex 15 |
| Salts amount | 0 | 1.67% | 5.01% | 3.24% | 9.72% |
| CPL color | transparent | Light yellow | Light yellow | Light yellow | Light yellow |
| GC purity | 99.5% | 99.2% | 99.1% | 99.4% | 98.6% |
| Peaks of lights | 5 | 9 | 7 | 8 | 6 |
| Peaks of heavies | 2 | 3 | 5 | 4 | 3 |
| Total number of peaks | 7 | 12 | 12 | 12 | 9 |

As can be concluded from the presented results the conversion and yield of 6-ACA to caprolactam did not suffer negative impacts in the process of the disclosure even when the possible contaminants were present in the starting material at much higher levels as is the usual content of inorganic and organic salts. Also the quality of caprolactam remained at usual level: the yellowish color present at higher concentration of contaminants can suggest the presence of few ppm of byproducts coming from the contaminants.

The lower yield observed in the example 15 seems to depend more on the lower temperature rather than on the higher amount of salts.

Example 16

One additional trial was made with the combination of possible all types of contaminants coming from fermentation during the production of the bio-based 6-ACA. The combination of sugars, inorganic salts, and organic salts was realized at the maximum level of each family of contaminants.

In table 11 the mix of all contaminants is summarized.

TABLE 11

| Sugar | Ex 16 |
|---|---|
| Sugars (Mix of Ex. 11) | 3.40% |
| Inorganic salts (Mix of Ex. 12) | 1.67% |
| Organic salts (Mix of Ex. 14) | 3.24% |
| Total % on dry 6-ACA | 8.31% |
| Total dosage of mix | 1.00 |

The trial with the mix of all contaminants sugars, inorganic and organic salts was performed with the same procedure as used in the Example 4 to evaluate conversion and yield of the 6-ACA to equivalent caprolactam in the process of the disclosure. At same time the quality of the raw caprolactam was checked. The results are presented in the table 12.

TABLE 12

Trials with all contaminants

|  |  |  | Example | |
|---|---|---|---|---|
|  |  |  | Ex. 8 Ref. | Ex. 16 |
| Load in Step (i) | 6ACA | [kg] | 25 | 25 |
|  | H2O | [kg] | 6.25 | 6.25 |
|  | Total sugars | [%] | 0 | 3.40% |
|  | Total inorganic salts mix | [%] | 0 | 1.67% |
|  | Total organic sals | [%] | 0 | 3.24% |
| Load in Step (ii) | Caprolactam | [kg] | 57.6 | 57.6 |
|  | Oligomers | [kg] | 6.4 | 6.4 |
|  | Catalyst H3PO4 on total | % | 4 | 4 |
| Output mass | Caprolactam | [kg] | +22.8 | +25.3 |
|  | Oligomers | [kg] | −1.2 | −3.7 |
|  | 6ACA | [kg] | −25 | −25 |
|  | 6ACAtoCPLyield | [%] | 100 | 100 |
| Results | Average T in Step (ii) | [° C.] | 256 | 256 |
|  | Reaction Time | [h:min] | 04:1 | 04:45 |

For each trial the total distribution of the Inlet and Outlet mass was the same or similar as indicated in the mass balance of Example 4, with the mixture of total salts loaded in the preparation reactor R1 of step (i).

The caprolactam produced was collected in a vessel and analyzed via gas chromatography. The results are presented in table 13.

TABLE 13

|  | Example | |
|---|---|---|
|  | Ex 8 Ref | Ex 16 |
| Sugars | 0 | 3.40% |
| Inorganic salts | 0 | 1.67% |
| Organic salts | 0 | 3.24% |
| Total contaminats | 0 | 8.31% |
| CPL color, visual aspect | transparent | Light brown |
| GC purity | 99.5% | 99.4% |
| Peaks of lights | 5 | 11 |
| Peaks of heavies | 2 | 4 |
| Total number of peaks | 7 | 15 |

As can be concluded from the presented results the conversion and yield of 6-ACA to caprolactam also with mixing all possible types of contaminants did not suffer negative impacts in the process of the disclosure. Also the quality of caprolactam remained at the usual level: the brownish color at higher concentration of contaminants can suggest the presence of few ppm of byproducts coming from the contaminants.

Examples 17-20

Following the same procedure as used in the Example 4, some trials have been performed with different catalysts instead of phosphoric acid, in order to evaluate their catalytic effect in the process of the disclosure.

The evaluation was done by measuring:
Conversion of 6ACA;
Yield of 6-ACA to caprolactam;
Quality of the raw caprolactam obtained.

Each catalyst was added in an amount equivalent to the amount in moles of the phosphoric acid used in the procedure of the Example 4. The results are presented in table 14.

TABLE 14

|  |  |  | Example | | | | |
|---|---|---|---|---|---|---|---|
|  |  |  | Ex 8 Ref | Ex 17 | Ex 18 | Ex 19 | Ex 20 |
| Load in Step (i) | 6ACA | [kg] | 25 | 25 | 25 | 25 | 25 |
|  | H2O | [kg] | 6.25 | 6.25 | 6.25 | 6.25 | 6.25 |
| Load in Step (ii) | Caprolactam | [kg] | 57.6 | 57.6 | 57.6 | 57.6 | 57.6 |
|  | Oligomers | [kg] | 6.4 | 6.4 | 6.4 | 6.4 | 6.4 |
|  | H3PO4 | [% on tot. mass] | 4 | — | — | — | — |
|  | Diammonium phosphate | [% on tot. mass] | — | 5.4 | 5.4 | — | — |
|  | Boric acid | [% on tot. mass] | — | — | — | 2.5 | — |
|  | p-toluenesulfonic acid | [% on tot. mass] | — | — | — | — | 7 |
| Output mass | Caprolactam | [kg] | +22.8 | +25.6 | +23.9 | +7.0 | +23.2 |
|  | Oligomers | [kg] | −1.2 | −4.0 | −2.3 | +14.6 | −1.6 |
|  | 6ACA | [kg] | −25 | −25 | −25 | −25 | −25 |
| Results | 6ACA to CPL yield | [%] | 100 | 100 | 100 | 32.5 | 100 |
|  | Average T in Step (ii) | [° C.] | 256 | 250 | 260 | 257 | 252 |
|  | Reaction time | [h:min] | 04:10 | 05:15 | 04:05 | 04:30 | 04:45 |

The caprolactam produced in each trial was collected in a vessel and analyzed via gas chromatography and pH. The results are presented in table 15.

TABLE 15

| | Example | | | | |
|---|---|---|---|---|---|
| | Ex 8 Ref | Ex 17 | Ex 18 | Ex 19 | Ex 20 |
| Catalyst | $H_3PO_4$ | Diammonium phosphate | Diammonium phosphate | Boric acid | p-toluenesulfonic acid |
| CPL color | transparent | transparent | transparent | transparent | transparent |
| GC purity | 99.5% | 99.4% | 99.2% | 99.1% | 99.1% |
| Peaks of lights | 5 | 8 | 7 | 4 | 7 |
| Peaks of heavies | 2 | 2 | 2 | 2 | 2 |
| Total number of peaks | 7 | 10 | 9 | 6 | 9 |
| pH | 5.6 | 8.9 | 8.6 | 5.1 | 5.1 |

As can be concluded from the presented results, the process of the disclosure could work also with different catalysts.

With diammonium phosphate the reaction proceeds the same way as with phosphoric acid; furthermore, it is once again verified the effect of the temperature on the kinetics and therefore on the reaction time.

With boric acid the yield is lower because the reaction proceeds, but with a slower kinetics.

About the quality, the main difference is in the pH of the raw caprolactam obtained with diammonium phosphate, which is basic instead of acid.

Example 21

(three step continuous process at an industrial scale, in order to evaluate the scale up of the process described in the examples from 2a to 20, with the amount of catalyst kept at 4 wt. %, as in the examples from 4 to 20).

Step (i).

In an industrial reactor made in stainless steel, called pre-reactor, having a volumetric capacity of 9 m³ and provided with temperature control (i.e. Unit R1), a higher amount of 6-ACA than the pilot trials was fed.

The reactor was fed with the following total materials:
6ACA, powder: 975 kg
Solution caprolactam/water, with 75 wt. % of caprolactam: 496 kg.
The total composition loaded in the industrial reactor was:

TABLE 16

| | [kg] | [wt. %] | Ratio 6-ACA/CPL |
|---|---|---|---|
| 6-ACA powder | 975 | 66.3 | 72.4:27.6 |
| CPL | 372 | 25.3 | |
| $H_2O$ | 124 | 8.4 | |
| Total load | 1471 | 100.0 | |

The solid material is 72 wt. % of 6-ACA and 28 wt. % caprolactam; water is about 8 wt. % of the total weight.

The reactor was then heated adiabatically reaching the following conditions, i.e. maintenance conditions:
pressure: 9.4 bar;
temperature: 202° C.

The mixture was kept on these conditions for a maintenance time of 30 minutes, and all the material was transferred to a cyclization reactor in step (ii), in the same manner and with the same effects explained in the previous Example 2a.

As soon as the transfer in the cyclization reactor was completed, the operations hereinabove described are repeated in the same manner, in order to increase with a multistep sequence, the amount of 6-ACA to obtain a continuous process for the step (ii). In this example, however, only two cycles in step (i) were considered.

Step (ii).

The cyclization reactor (i.e. unit R2) made in stainless steel, having a volumetric capacity of 22 m³ and a means for thermal control, was prepared and brought to the working conditions.

The stirring inside the reactor was guaranteed by the continuous feeding of the superheated steam through an annular series of steam jets located at the bottom.

Into the reactor an initial load of CPL oligomers was fed to keep the level at a known measured and controlled optimal value and phosphoric acid in the amount of 4.0 wt. % based on the total mass in the cyclization reactor (see Table 17 which presents schematic mass balance calculation at the end of Example 21).

The liquid catalyst $H_3PO_4$ with concentration of 85 wt. % in water was fed into the cyclization reactor continuously varying the flow rate according to the chemical analysis results in order to have the catalyst inside the reactor always at about 4 wt. %, to guarantee its presence in the reacting mixture all the time during the trial.

The reactor was heated up to T=256° C. by action of the diathermic oil circulation in the external jacket, maintained at atmospheric pressure.

The flash of the water when the material was transferred caused a short initial temporary temperature decrease (down to 237° C.), followed by the increase given by the heating (up to 252° C.), while the overheated steam was continuously fed at constant rate through controlled flow of about 1300 kg/h to the reactor.

The 6-ACA inside the reactor underwent the cyclization reaction, with the production of CPL: as soon as the CPL was formed it was stripped away by the superheated steam to step (iii).

After transferring gradually the materials from R1 to the cyclization reactor, the level in R2 increased. The cyclization reaction was considered finished when the level returned as it was before the transferring of material from R1.

Step (iii).

The vapors as mixture of water steam and caprolactam coming from the cyclization reaction of 6ACA were continuously sent to a packed bed rectification column (i.e. Unit C1), with condenser and without boiler since the heat for rectification was recovered from the energy delivered in the previous step. As cooling and condensation medium some liquid water was fed to the higher part of the column.

During the reaction, from the top of the column the water steam was at 100-105° C. practically without any caprolactam and was sent directly to condensate through a tower water condenser, while from the bottom of the column a concentrate caprolactam water solution at 110-120° C. was collected and stored into a storage vessel until the cyclization reaction was finished, as described in step (ii).

Mass balance and analytical results are summarized in the following tables:

Mass Balance

TABLE 17

|  | FEED | | Equivalent CPL | Raw CPL Collected bottom C1 | | Total raw |
| --- | --- | --- | --- | --- | --- | --- |
|  | kg | wt. % | kg | kg | wt. % | CPL |
| 6-ACA loaded | 975 | 72.4 | 841 | — | — |  |
| CPL loaded | 372 | 27.6 | 372 | — | — |  |
| Raw CPL Solution | — | — | — |  |  |  |
| Total mass | 1347 | 100.0 | 1213 | 1620 | 79.4 | 1286 |

The data are confirming that:
a) also at an industrial scale, the cyclization of 6-ACA had a 100% conversion to raw CPL with yield 100%;
b) in the specific case, even if the kinetics was lower than the 6-ACA in the selected conditions, also few CPL oligomers initially loaded for the start up of the reactor were converted to raw CPL.

Checking the residual material in the R2 by analysis it was found the initial composition of CPL oligomers with 3-4% of catalyst $H_3PO_4$.

Analysis

TABLE 18

| 6ACA to CPL yield | [%] | 100 |
| --- | --- | --- |
| Average temperature | [° C.] | 242 |
| Reaction time | [h:min] | 02:33 |
| GC purity | [%] | 99.6 |
| GC light peaks-GC heavy peaks |  | 10-2 |

From the results it comes out that the cyclization process of 6-ACA to obtain caprolactam as described can work even at an industrial scale also with the amount of water in the feed lower than 20 wt. %, in this case 8 wt. %

Example 22

(three step continuous process at an industrial scale like Example 21 but using 100% 6ACA)

Following a similar procedure as that used in Example 21, another run was conducted by feeding the pre-reactor with 6ACA and water without caprolactam.

The following materials were loaded:
6ACA, powder: 1150 kg;
Water: 200 kg (about 15 wt. % of the total weight in the pre-reactor).

The total composition loaded in the industrial reactor was:

TABLE 19

|  | kg | % | Ratio 6-ACA/CPL |
| --- | --- | --- | --- |
| 6-ACA powder | 1150 | 85.2 | 100:0 |
| CPL | 0 | 0 |  |
| H2O | 200 | 14.8 |  |
| Total load | 1350 | 100.0 |  |

Mass balance and analytical results are summarized in the following tables:

Mass Balance

TABLE 20

|  | FEED | | Equivalent CPL | Raw CPL Collected bottom C1 | | Total raw |
| --- | --- | --- | --- | --- | --- | --- |
|  | kg | wt. % | kg | kg | wt. % | CPL |
| 6-ACA loaded | 1150 | 100 | 992 | — | — |  |
| CPL loaded | 0 | 0 | 0 | — | — |  |
| Raw CPL Solution | — | — | — | — | — |  |
| Total mass | 1150 | 100 | 992 | 1340 | 73.1 | 979.6 |

Also using only 6-ACA in the feed, the data were again confirming that at an industrial scale the cyclization of 6-ACA is 100% converted to raw CPL with yield 100%. Checking the residual material in the R2 by analysis it was found the initial composition of CPL oligomers with 3-4% of catalyst $H_3PO_4$.

Analysis

TABLE 21

| Example 22 | | |
| --- | --- | --- |
| 6ACA to CPL yield | [%] | 100 |
| Average temperature | [° C.] | 240 |
| Reaction time | [h:min] | 3:00 |
| GC purity | [%] | 99.6 |
| GC light peaks-GC heavy peaks |  | 11-1 |

The results of this run gave a confirmation of what reported in Example 21: the cyclization process of 6-ACA to obtain caprolactam as described can work even at an industrial scale, also with the amount of water in the feed lower than 20%, in this case 15% and also by using 100% of 6ACA as solid material in the feeding.

The invention claimed is:

1. A process for the production of epsilon caprolactam from 6-aminocaproic acid, the process including the following steps:
   step (i)—pre-treating a starting material comprising 6-aminocaproic acid in order to prepare it for step (ii)—the cyclization, whereby the starting material is pre-heated to the temperature in or near the temperature of a cyclization reactor of step (ii) to accelerate a cyclization reaction in step (ii);
   step (ii)—feeding the pre-treated starting material obtained in step (i) under a controlled flow rate into a cyclization reactor and continuously contacting said starting material with a constant flow of superheated steam in the presence of a catalyst, wherein cyclization of 6-aminocaproic acid to epsilon caprolactam occurs and wherein stream-stripping of a vapor mixture comprising epsilon caprolactam and water occurs continuously with the superheated steam, wherein the cyclization reactor is at a pressure and temperature favouring cyclization and steam-stripping;
   step (iii)—condensing the vapour mixture comprising epsilon caprolactam and water obtained from step (ii) to obtain an aqueous solution of epsilon caprolactam;
   wherein in step (i) the starting material comprises:
   6-aminocaproic acid in a form of a solution in water with the concentration of 6-aminocaproic acid at least 50 wt. % based on the total mass of the starting material; or
   6-aminocaproic acid in an isolated powdered form, wherein said starting material is heated in a pre-melter to a temperature of 210-260° C., whereby a molten 6-aminocaproic acid with no water is obtained and is then fed into the cyclization reactor of step (ii).

2. The process according to claim 1, wherein the temperature of pre-treating in step (i) is in the range from 170-260° C.

3. The process according to claim 1, wherein the temperature of pre-treating in step (i) is in the range from 190-200° C.

4. The process according to claim 1, wherein the formation of vapours causes an increase of pressure in step (i) up to 8-10 bars.

5. The process according to claim 1, wherein said aqueous solution is maintained in these conditions until water in the pre-treated aqueous solution is in condition to flash immediately and to be transformed into steam, when said solution is fed into the cyclization reactor of step (ii).

6. The process according to claim 1, wherein said aqueous solution is maintained in said conditions for at least 30 minutes.

7. The process according to claim 1, wherein the cyclization reactor is for the start up phase brought at a pressure and temperature favouring cyclization and steam-stripping, by feeding the cyclization reactor with an initial load of a caprolactam solution and a catalyst, prior the pre-treated starting material from step (i) is fed into the cyclization reactor.

8. The process according to claim 7, wherein the concentration of catalyst in the initial load is from 3 to 4 wt. % calculated on the mass of the initial load.

9. The process according to claim 1, wherein the cyclization reactor is at atmospheric pressure or at slightly elevated pressure, i.e. in the range from 1.0 to 1.5 bar, and at temperature in the range from 220 to 350° C.

10. The process according to claim 1, wherein the superheated steam has a temperature in the range of 300-450° C.

11. The process according to claim 1, wherein the superheated steam is continuously fed through an annular series of steam jets located at the bottom of the cyclization reactor.

12. The process according to claim 1, wherein the catalyst is present in the cyclization reactor in the amount from 1 to 10 wt. %, calculated on the total mass in the cyclization reactor.

13. The process according to claim 1, wherein the catalyst is present in the cyclization reactor in the amount from 1 to 8 wt. %, calculated on the total mass in the cyclization reactor.

14. The process according to claim 1, wherein the catalyst is present in the cyclization reactor in the amount from 3 to 4 wt. %, calculated on the total mass in the cyclization reactor.

15. The process according to claim 1, wherein the required amount of catalyst in the cyclization reactor is maintained by a periodical addition of fresh catalyst based on periodical chemical analysis of the samples of the reaction mass taken from the reactor, wherein fresh catalyst is added when the concentration of the catalyst inside the reactor falls below 2 wt. % calculated on the total mass in the cyclization reactor.

16. The process according to claim 1, wherein the catalyst is selected from:
   phosphoric acid, phosphorous acid, poly-phosphoric acid with short chain, ammonium phosphoric acid, and any phosphoric salt, including metal salts, able in the process conditions to deliver the strong acid group —P—OH;
   boric acid and its salts;
   para-toluenesulphonic acid and its salts; and
   phosphotungstic acid.

17. The process according to claim 16, wherein the catalyst is selected from:
   phosphoric acid and poly phosphoric acids with short chains;
   ammonium mono-, di- and tri-phosphates;
   sodium mono-phosphate and potassium mono-phosphate;
   boric acid and its mono-ammonium salt;
   p-toluenesulfonic acid and its mono-ammonium salt; and
   phosphotungstic acid.

18. The process according to claim 16, wherein the catalyst is phosphoric acid.

19. The process according to claim 1, wherein the flow rate of the superheated steam in step (ii) is within the range which ensures that the ratio of water to caprolactam in the vapours exiting the cyclization reactor is kept in the range of 65-35 w/w.

20. The process according to claim 19, wherein the flow rate of the superheated steam is in the range of 1.3-1.8 kg per kg of 6-aminocaproic acid which enters the cyclization reactor.

21. The process according to claim 1, wherein in step (iii) additionally concentration of the aqueous solution of epsilon caprolactam is done.

22. The process according to claim 1, wherein the condensation and concentration is done simultaneously in a condensation-rectification column, wherein an aqueous solution of epsilon caprolactam with the concentration richer in caprolactam than in the vapour phase is collected at the bottom of the condensation-rectification column and low pressure steam at the top of the condensation-rectification column.

23. The process according to claim 22, wherein the concentration of caprolactam solution is in the range from 25-85 wt. %.

24. The process according to claim 1, wherein the condensation-rectification column works at atmospheric pressure and the temperature profile at the bottom of the column is maintained in a range of 115-125° C. and on the top of the column at approx. 100-102° C.

25. The process according to claim 1, wherein water condensation heat recovered by condensing the vapours of caprolactam and water coming from the cyclization reactor of step (ii) is reused in the plant facility.

26. The process according to claim 1, wherein the heat necessary for the concentration is supplied from the vapours in the step (ii).

27. The process according to claim 1, wherein 6-aminocaproic acid is obtained either from traditional petro chemical processes or from biochemical processes, wherein higher amounts of carbohydrates are comprised in 6-aminocaproic acid.

28. The process according claim 27, wherein the carbohydrate concentration in the 6-aminocaproic acid is up to 15 wt. %, based on the mass of the 6-aminocaproic acid.

29. The process according to claim 27, wherein carbohydrate concentration in the 6-aminocaproic acid comprises at least 12.5 wt. %, 10 wt. %, 5 wt. %, 4 wt. %, 3.5 wt. %, 3.4 wt. %, 3 wt. %, 2 wt. % or 1 wt. % and up to 15 wt. %, 12.5 wt. %, 10 wt. %, 5 wt. % or 4 wt. % of carbohydrate, based on the mass of the 6-aminocaproic acid.

30. The process according to claim 1, wherein the process is carried out batchwise or continuously.

\* \* \* \* \*